United States Patent
Futamura et al.

[11] Patent Number: 5,392,359
[45] Date of Patent: Feb. 21, 1995

[54] APPARATUS FOR INSPECTING APPEARANCE OF CYLINDRICAL OBJECTS

[75] Inventors: Tsuyoshi Futamura, Tokyo; Hiroyoshi Suda, Kanagawa; Minoru Fujita, Kanagawa; Kouzou Ichiba, Kanagawa, all of Japan

[73] Assignees: Japan Tobacco, Inc., Tokyo; Toshiba Engineering Corporation, Kanagawa, both of Japan

[21] Appl. No.: 996,401

[22] Filed: Dec. 23, 1992

[30] Foreign Application Priority Data

Dec. 27, 1991 [JP] Japan .................. 3-347080

[51] Int. Cl.⁶ ........................... G06K 9/00
[52] U.S. Cl. .................... 382/8; 209/536; 348/92; 348/128; 382/30
[58] Field of Search ............... 382/8, 1, 30; 209/939, 209/522, 535, 536; 356/239, 240, 237; 250/223 B; 358/106, 107, 101; 348/86, 92, 128, 127

[56] References Cited

U.S. PATENT DOCUMENTS

| | | | |
|---|---|---|---|
| 4,859,863 | 8/1989 | Schrader et al. | 382/8 |
| 4,920,572 | 4/1990 | Sugita et al. | 382/8 |
| 5,007,096 | 4/1991 | Yoshida | 382/8 |
| 5,204,911 | 4/1993 | Schwartz et al. | 382/8 |
| 5,214,713 | 5/1993 | Juvinall | 382/8 |

Primary Examiner—Joseph Mancuso

[57] ABSTRACT

An apparatus for automatically inspecting abnormalities in the external surface of cylindrical objects. The apparatus inspects the appearance of a cylindrical object using image processing. The apparatus includes a transporter and a CCD camera. The transporter rotates the cylindrical object about an axis of the cylindrical object. The CCD camera picks up images showing the appearance of the inspected cylindrical object. The images include picture elements, and each picture element has a corresponding luminance. The apparatus further includes a controller. The controller generates at least one masking window to mask at least one predetermined portion of at least one image; generates at least one luminance sum for each image by adding, for each image, the luminance of a predetermined number of picture elements in unmasked portions of the image; compares each luminance sum to a predetermined threshold; and judges whether the cylindrical object includes a defect based on a result of each comparison.

11 Claims, 8 Drawing Sheets

APPARATUS FOR INSPECTING APPEARANCE OF CYLINDRICAL OBJECTS

BACKGROUND OF THE INVENTION

1. Field of the Invention

This invention relates to an apparatus for inspecting the appearance of cylindrical objects and more particularly to an apparatus for automatically inspecting abnormality in external surface, dirt on the surface, and poor shape of cylindrical objects by using image processing.

2. Description of the Prior Art

In industrial mass production, automation of producing and inspecting systems has been pushed ahead to rationalize the production process. The inspection of the appearance of products, which is one of the matters to be rationalized, is mainly performed through visual observation. However, in recent years with the spread of computers, it has developed that images which are picked up by a television camera (hereinafter merely called as "camera") are processed by a computer. The technic in which the picked up image is processed by the computer has been developed and adapted to automatically inspect the appearance of the products.

In the apparatus for inspecting the appearance with image processing, the images picked up by the camera are converted into analog signals. Then, the signals are converted into digital signals so as to be discriminated by the computer.

As a method of discriminating or inspecting the appearance with a computer, it has been generally used that an image of a standard product or an acceptable product (hereinafter merely called as "a standard image"), which is stored in the computer in advance, is compared with an image of an inspected object (hereinafter merely referred as "an inspected image"). Then, if there is a point or portion of the inspected image that does not correspond with the standard image, the inspected object relating to the inspected image is judged to be a defective. On the other hand, when the standard image and the inspected image coincide with each other, the inspected object relating to the inspected image is judged to be an acceptable product. In the discriminating method using such a standard image, even though characters or symbols are printed on the external surface of the inspected object, the inspecting operation can be carried out in consideration of the existence of the characters, symbols or the like.

Besides the above method, there is another method in which luminance signals of the image, which is picked up by the camera, are digitized and the luminance is integrated in a prescribed range to judge the inspected object as a defective product when the integrated luminance falls below (or is less than) a predetermined threshold.

As described above, in the method of comparing the standard image with the inspected image, an entrapping start point and a finishing point must always coincide with those of the standard image, and the inspected object is limited to be a polygon with symmetrical shape.

When the appearance of the cylindrical object is inspected based on the image picked up by the camera, an overall image of the object including external periphery should be entrapped. As described above, in the method of inspecting the appearance of the cylindrical object, the inspected object is rotated while the camera being fixed or the camera is rotated about the inspected object to pick up the appearance of the inspected object. The method in which the inspected object itself is rotated while the camera is fixed is preferable since in the other method, mounting and rotating mechanisms for the camera become rather complicated.

Further, in the method of rotating the inspected object, the rotating operation should change in accordance with the diameter of the inspected object. That is, when the diameter is small, the inspected object is preferably rotated with an axis of the horizontally laid inspected object. Otherwise, the structure for maintaining and supporting the inspected object becomes complicated.

However, in the method of inspecting the appearance of the cylindrical object by entrapping the overall image of the object, it is difficult to compare the inspected image with the standard image since the start point of entrapping the inspected object does not always coincide with that of the standard image.

That is, in mass production of the cylindrical object, the appearance of the inspected objects must be inspected while the object is automatically transported by conveyors or the like. Therefore, it is difficult to fix the start point of the image of the inspected object at the inspection of the appearance thereof due to the mechanism of the transporter. To eliminate the problem, not only will the transporting mechanism become complicated but also the speed of the inspection will be decreased.

As a result, it is proposed that the luminance of the inspected object is summed up to inspect the appearance of the cylindrical object, which requires the appearance inspection consider of characters or symbols on the outer periphery of the inspected object.

SUMMARY OF THE INVENTION

It is therefore an object of the present invention to provide an apparatus for inspecting the appearance of cylindrical objects on which characters or symbols are printed at the outer periphery thereof to judge defective objects.

The apparatus for inspecting the appearance of the cylindrical object according to the present invention comprises: rotating means for rotating the cylindrical object about an axis of the cylindrical object; picking up means for picking up images showing the appearance of the inspected object which are axially and circumferentially divided into a predetermined number; masking window generating means for generating masking windows for masking characters and symbols which are printed on an axially predetermined portion of the divided picked-up images of the inspected object; detecting window generating means for generating detecting windows for extracting portions on the axially predetermined portion of the divided picked-up images of the inspected object on which the characters and symbols are not printed; adding means for adding luminance excluding the luminance of the masking window for each of the divided picked-up images each; and comparing means for comparing the added luminance with a predetermined threshold, wherein a portion where the added luminance falls below (or is less than) the threshold is judged to be defective.

It is another object of the present invention to provide the apparatus for inspecting the appearance of a cylindrical object described above which further comprises subdivided windows which are obtained by further subdividing the detecting windows and counting means for counting the number of windows having luminance which falls below (or is less than) exceed a predetermined threshold (which is independently set for each of the subdivided windows); and wherein the appearance of the cylindrical object is judged to be defective when the number of windows exceeds a predetermined number.

In the apparatus for inspecting the appearance of a cylindrical object according to the present invention, the cylindrical object being inspected is rotated about the axis of the object so that the appearance of the object is picked up by a camera or the like. At that time, the appearance of the inspected object is circumferentially divided into a predetermined number, and the predetermined number of axially divided images are picked up. Further, masking windows mask characters and symbols printed on certain portions of the inspected object and adding means add luminance of the windows excluding masked windows for each of the divided picked-up images. Then, when the sum of the luminance falls below (or is less than) the threshold, corresponding portions are judged to be defective.

BRIEF DESCRIPTION OF THE DRAWINGS

The present invention will be more apparent from the following description with reference to the accompanying drawing wherein.

DETAILED DESCRIPTION OF PREFERRED EMBODIMENTS

Figure 1:
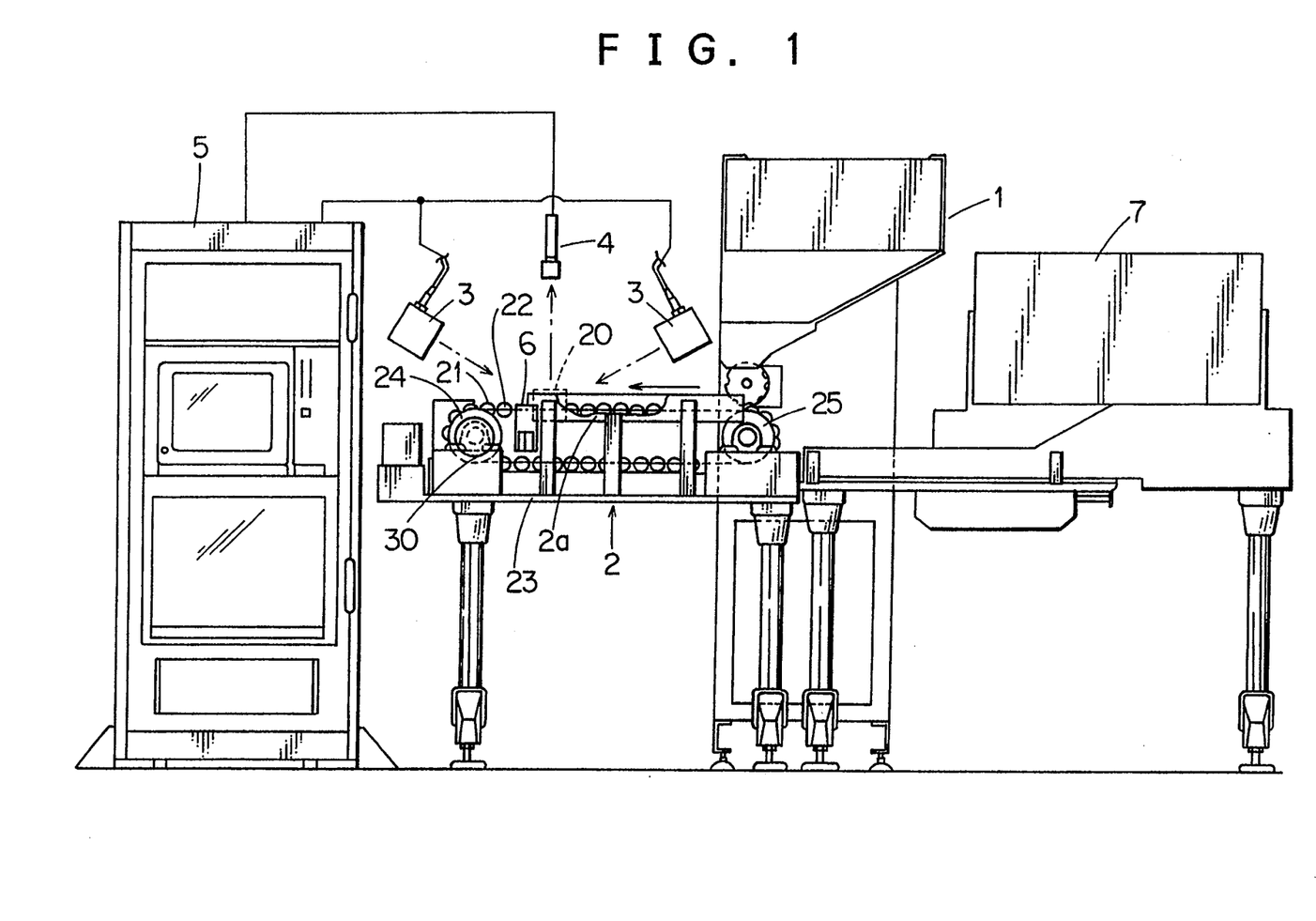
FIG. 1 is a schematic view of a transporter using an inspection apparatus according to an embodiment of the present invention.

FIG. 1 is a schematic view of a cigarette transporter with an appearance inspecting apparatus for a cylindrical object according to an embodiment of the present invention.

In the figure, reference numeral 1 is a hopper, 2 a transporter, 3 stroboscopes, 4 a CCD camera, 5 a controller, 6 a removing device, and 7 a pool. A cigarette is fed to a transporting route 2a of the transporter 2 from the hopper 1 one after another. At one end of the transporting route 2a is formed an inspecting section where a pair of stroboscopes 3 emits flush light to the transported cigarette and an image of the cigarette is picked up by the CCD camera 4.

Then, defects of the cigarette are detected by the controller 5 based on the image information, and cigarettes which are judged to be defective are removed by the removing device 6 such as an air nozzle. Nondefective cigarettes are transported by the transporter 2 to the pool 7 where the cigarettes are stocked.

Reference numeral 21 are rotating rollers, 22 a chain, 23 a frame, 24 and 25 sprockets, and 30 a rotary encoder. The sprocket 24 is rotated by a driving source not shown to move the chain 22 and the rotating roller 21 in the direction as indicated by an arrow. The rotating rollers 21 move by being rotated on a guide not shown on the transporting route. This causes the cigarettes between the rotating rollers 21 to move while being rotated.

Figure 2:
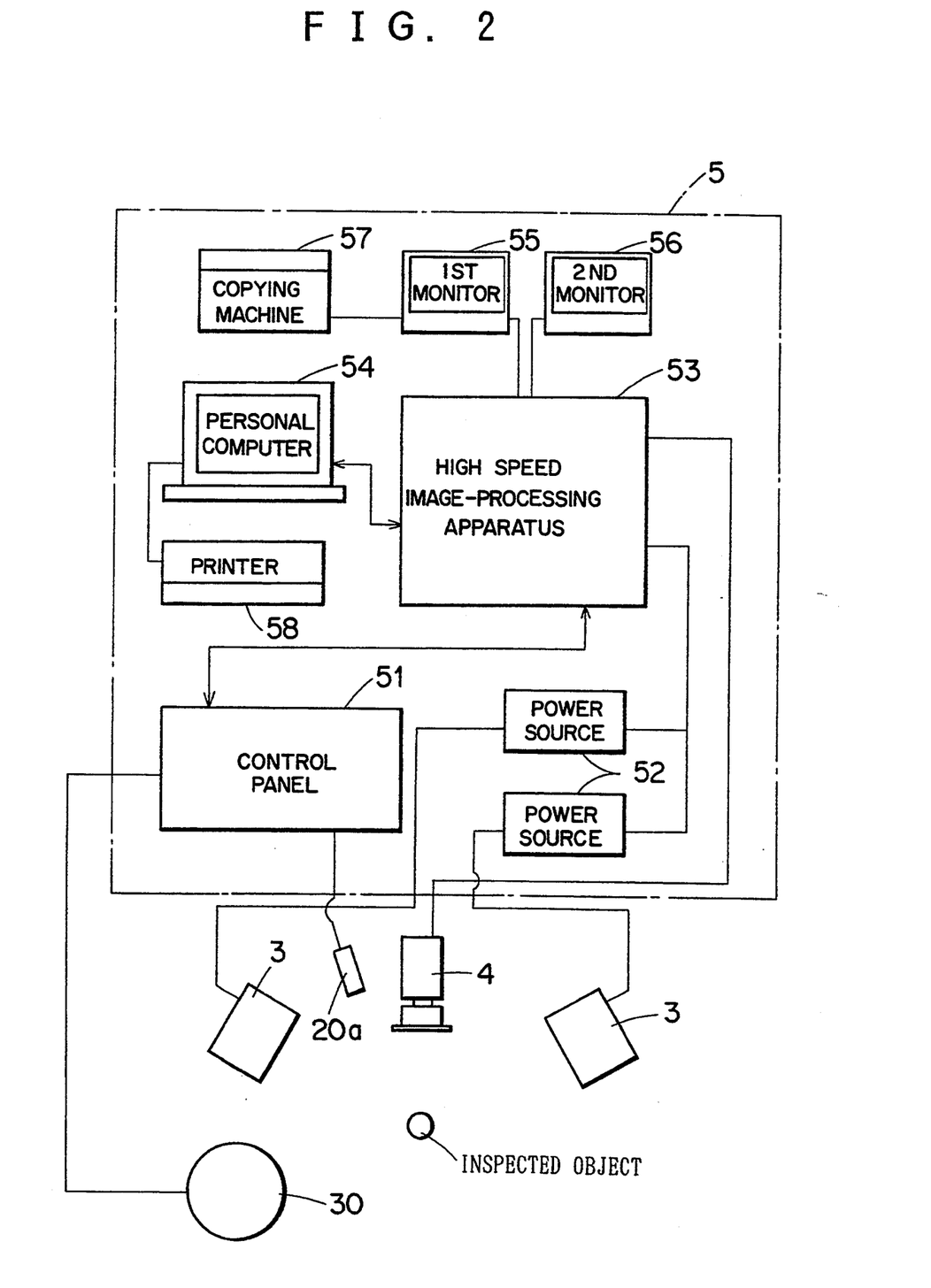
FIG. 2 is a block diagram of a controller according to an embodiment of the present invention.

In the transporter described above, the image information picked up by the CCD camera at the inspection section 20 is image-processed by the controller 5. The controller 5 comprises, as illustrated in FIG. 2, a control panel 51, power sources 52 of the stroboscopes, a high speed image-processing apparatus 53, a personal computer 54, a first monitor 55, a second monitor 56, a video hard copying machine 57, and a serial printer 58.

To the control panel are inputted detecting signals for detecting cigarettes from a reflective photoelectric sensor 20a, pulse signals from the rotary encoder 30, and defective product detecting signals from the high speed image-processing apparatus 53. On inputting the detecting signal to the control panel from the reflective photoelectric sensor 20a, a command signal for causing the stroboscopes 3 to emit light for the high speed image-processing apparatus 53 on a controlled cycle and another command signal for starting the pick up of the image are outputted, and the pulse signals from the rotary encoder 30 are outputted to the high speed image-processing apparatus 53 to allow the stroboscope 3 to emit pulse light.

The high speed image-processing apparatus 53 reads the image data out of the CCD camera 4 in synchronization with timings that the stroboscopes 3 emit light and the image data for a single cigarette is stored in a range which is set in advance. Further, on starting the entrapping of the image, a detecting signal is output to the personal computer 54. To the first monitor 55, an image is output in which the luminance of the entrapped image are processed and to the second monitor 56, analog signals are output from the CCD camera 4.

The timing that the stroboscopes 3 emit light is calculated from the rotary encoder 30 which is attached to a driving shaft of the sprocket 24. The cycle that the stroboscopes emit light, in other words, the intervals that the images are inputted are set at 37.5 micro seconds. The image of the cigarette is picked up while the image of the cigarette is divided into six equal sections for every 60 degree of rotating angle to obtain the overall image of the outer periphery of the cigarette.

Figure 3:
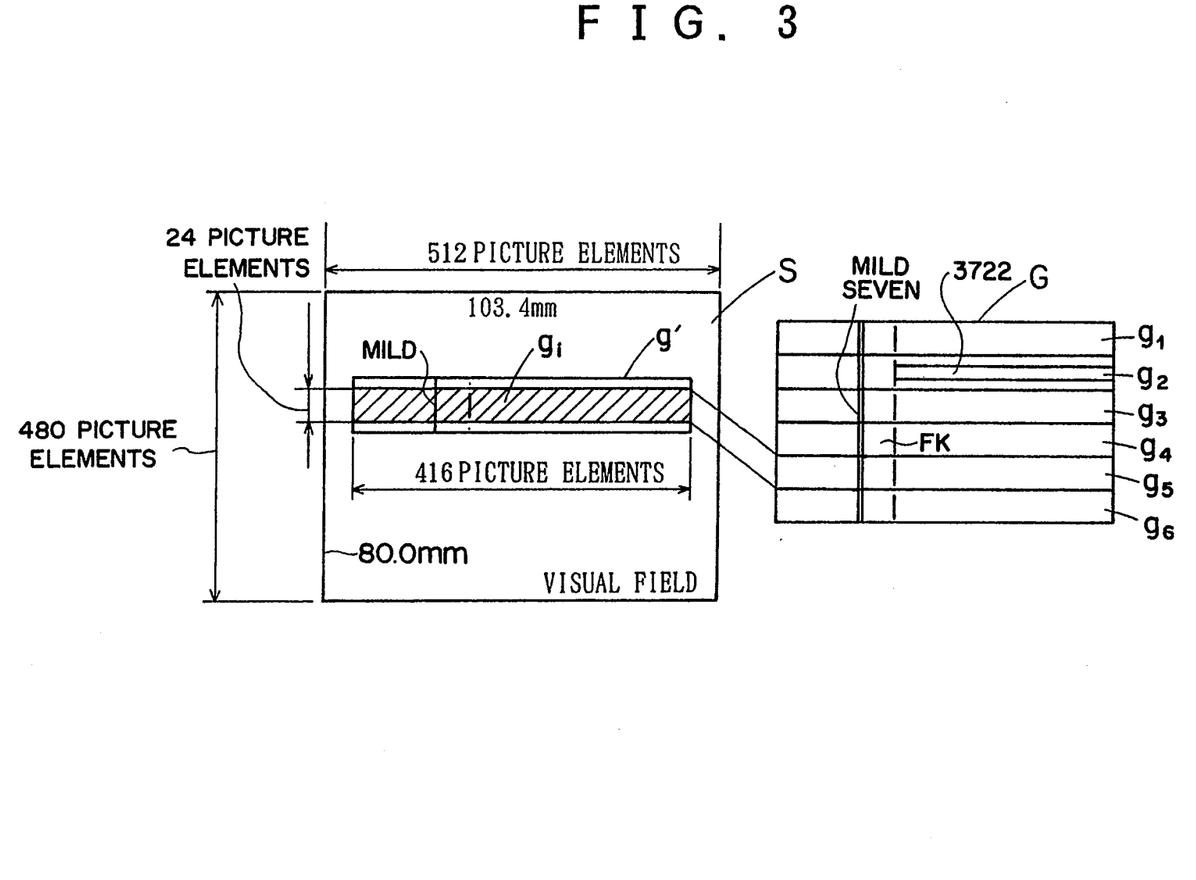
FIG. 3 shows the relation between an extracted image and an overall image of an inspected object according to the embodiment of the present invention.

The method of picking up the image will be explained in detail with reference to FIG. 3. An image gi is extracted from an image of the cigarette for a rotation angle of 60 degrees, which is picked up by the CCD camera 4 and is within a visual field of the camera 4. The extracted image gi covers a certain range about the axis of the image of the cigarette for the rotation angle of 60 degree. Images obtained for the rotation angle of 60 degrees are denoted g1 to g6, and a synthesized image G of the overall periphery of the cigarette is stored. The fault of each cigarette is checked based on these six images g1 to g6. In this embodiment, the visual field of the CCD camera 4 is 103.4 mm×80.0 mm and the width of the image thereof for the rotation angle of 60 degree corresponds to 24 picture elements.

Figure 4:
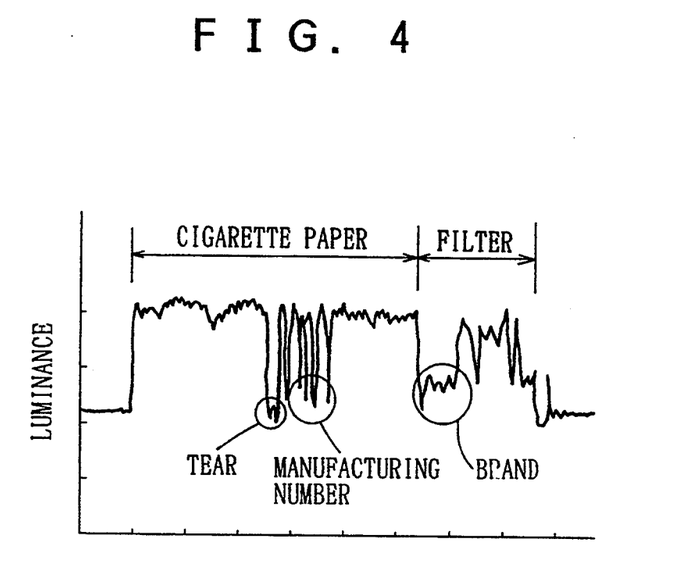
FIG. 4 is a graph showing luminance of image information of the inspected object according to the embodiment of the present invention.

Luminance signals of six images, for example, those of one horizontal line (512 picture elements) outputted from the CCD camera 4 are shown in FIG. 4. The luminance of white portions of the cigarette paper and filter becomes high and portions of the cigarette paper where manufacturing number is printed, or portions where the cigarette paper is torn, or portions of the filter where the brand is printed become low in luminance. Then, the luminance of each of the picture elements is converted into numerical data so as to be stored in the high speed image-processing apparatus 53.

Figure 5:
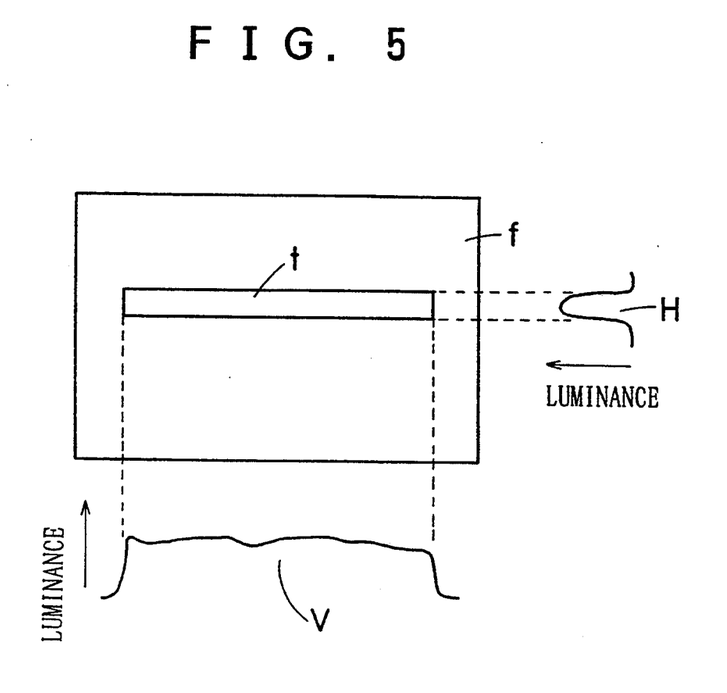
FIG. 5 is a graph showing luminance of the inspected object and background according to the embodiment of the present invention.

The luminance picked up by the CCD camera (i.e. the luminance of the picture elements) are horizontally or vertically added to obtain horizontal luminance information H and vertical luminance information V as shown in FIG. 5. This information shows that the luminance of a portion of the cigarette is different from that of other portions. The images extracted at the rising and falling of the horizontal or vertical information correspond to the images from g1 to g6. In other words, there is a characteristics in the horizontal and vertical information for every 60 degrees of the rotation angle, and the combination of the information will provide the information on the images from g1 to g6 to form the synthesized image illustrated in FIG. 3.

Abnormalities such as tear and dirt on a cigarette based on the luminance information, discoloration due to a heater (which may be generated while a pasted portion of the cigarette paper is dried by a heater), dirt due to ink which is used for printing characters or symbols on the cigarette paper, and dirt due to oil leakage from manufacturing machine are detected. The discoloration due to a heater is observed at a certain portion but the luminance of the portion is not decreased remarkably. Further, it is difficult to distinguish dirt in the characters or the symbols from the characters themselves.

Figure 6:
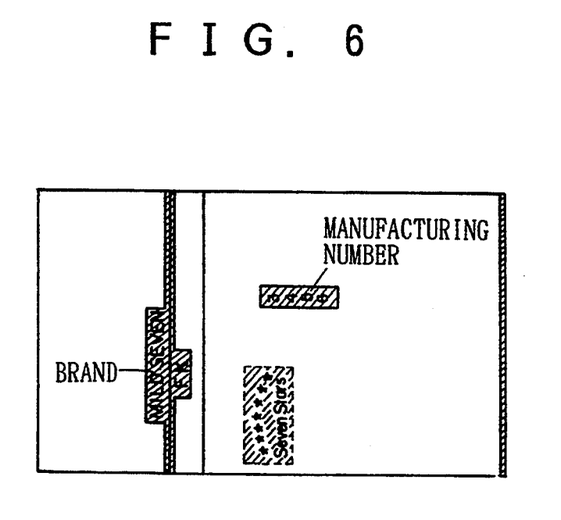
FIG. 6 shows masking windows for the inspection of cigarettes according to the embodiment of the present invention.

Therefore, as shown in FIG. 6, windows are required for extracting the luminance information of particular ranges or for masking the luminance information on the characters or symbols in accordance with inspected items.

Figure 7:
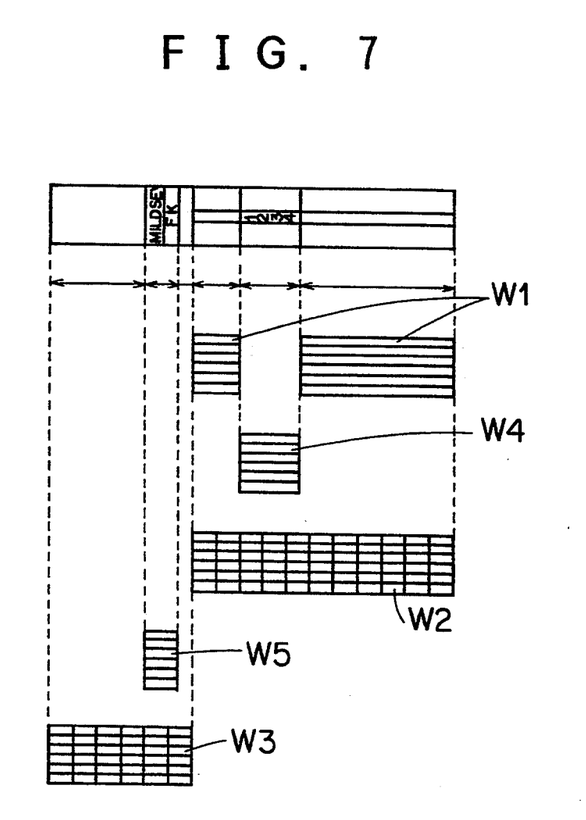
FIG. 7 shows windows for the inspection of cigarettes according to the embodiment of the present invention.

The explanation of the windows will be made with reference to FIG. 7. A heater discoloration window W1 is set at a portion of the cigarette paper excluding the portion where the manufacturing number is printed. A cigarette paper window W2 for detecting the dirt or tear of the cigarette paper is set at an area of the cigarette paper. Further, a filter window W3 for detecting the dirt on the filter is set at the filter area. A manufacturing number window W4 for masking the manufacturing number and a printing window W5 for masking the brand or the like are provided.

The cigarette paper window W2 and the filter window W3 are further divided vertically and horizontally to improve the discriminating operation. In other words, a large fault or a plurality of small faults on the cigarette paper may indicate the same sum of the luminance, as described below, which may cause a cigarette with small abnormality, which should be judged to be a nondefective, to be a defective product. To eliminate the problem, a number of small windows are used. The inspection of the cigarette is carried out with the windows for discriminating and masking as described below.

Figure 8:
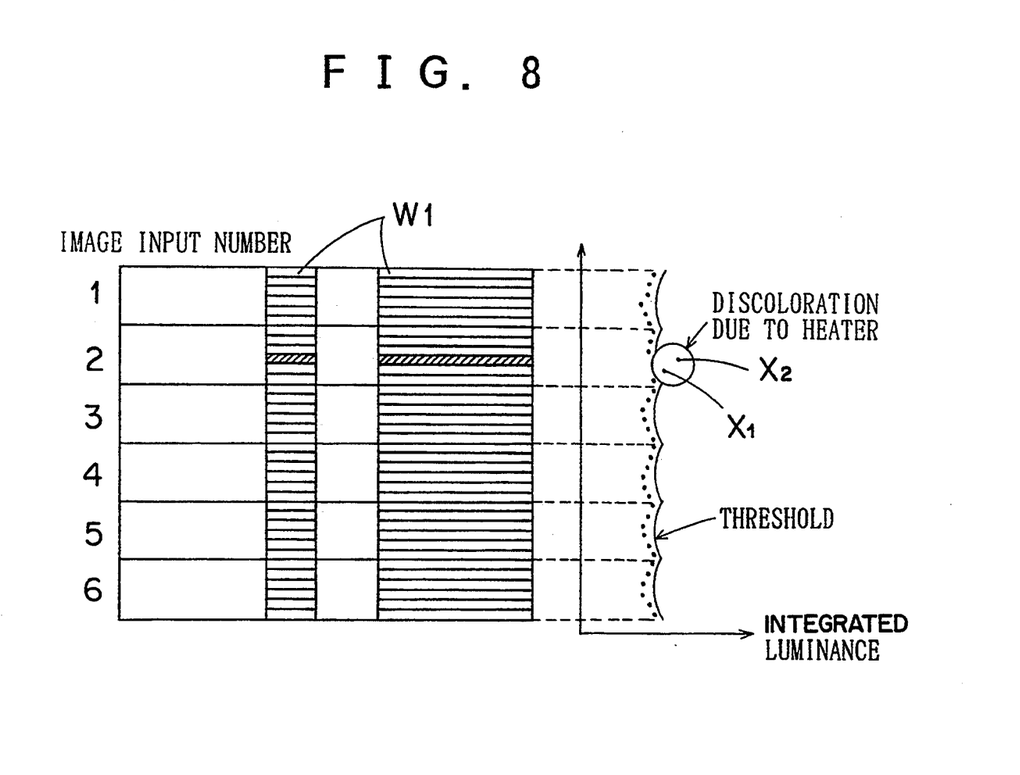
FIG. 8 shows the detection of discoloration due to heating of the cigarettes according the embodiment of the present invention.

In case of detecting the discoloration due to a heater, as illustrated in FIG. 8, the luminance of the picture elements each in the heater discoloration window which is located at a prescribed position of the visual field S, are added for each of the six images with input numbers 1 to 6. Specifically, as shown by the sub-windows in FIG. 8, the sum of the luminance for horizontally arranged picture elements are obtained. As a result, the sum of the luminance for each horizontal line in each of the images is obtained as indicated by the dots in the FIG. 8. Then, the sum is compared with a predetermined threshold also shown in FIG. 8. Since the discoloration due to the heater is observed in the image with input number 2, as illustrated in FIG. 8, the sum of the luminance X1, X2 each falls below (or is less than) the predetermined threshold and indicates discoloration due to the heater.

Figure 9:
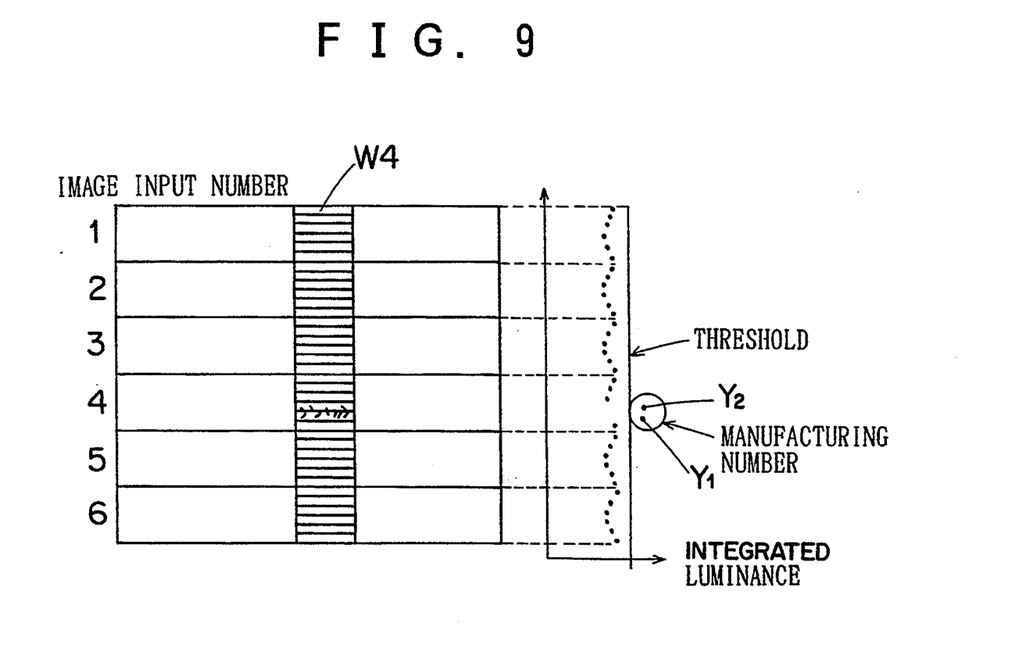
FIG. 9 shows detecting the manufacturing numbers of cigarettes according to the embodiment of the present invention.

Next, the method of detecting a tear of and dirt on the cigarette paper will be explained with reference to FIG. 9. The luminance of each picture element in the manufacturing number window W4, which is located in a prescribed position of the visual field S, are horizontal added for each of the six images with input numbers 1 to 6. Then, the sum of the luminance for each horizontal line in the images is calculated as indicated by dots in FIG. 9 so as to be compared with a predetermined threshold which is set in advance, also as shown in FIG. 9. When the manufacturing number is printed on the image, as with input number "4" as illustrated in the figure, the sums of the luminance Y1 and Y2, which fall below (or are less than) the predetermined threshold, are obtained to detect the window for masking the portion where the manufacturing number is printed.

Figure 10:
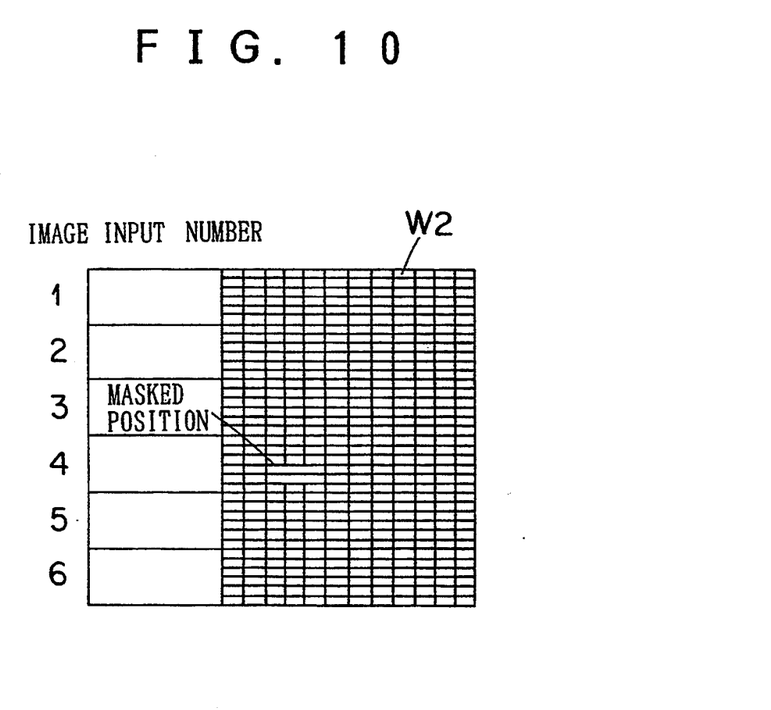
FIG. 10 shows detecting the defects on a paper roll of a cigarette according to the embodiment of the present invention.

Further, as illustrated in FIG. 10, the sum of the luminance of picture elements of windows, each of which is obtained by subdividing the cigarette paper window 2 for the six images with input numbers 1 to 6, is calculated for each subdivided window. When faults such as damage or tear, which indicate high very low luminance, are to be detected, a window corresponding to the manufacturing number is masked. Then, when the sum of the luminance of the other windows each falls below (or is less than) the prescribed threshold, the inspected object is judged to be defective. On the other hand, in order to detect faults such as a stain or a small amount of dirt, which indicates slightly low luminance, the luminance is summed up for each of the subdivided windows excluding a window corresponding to the manufacturing number. Then, the number of the subdivided windows having luminance sums which falls below (or are less than) the threshold is counted. When, the number of the subdivided windows having luminance sums which fall below (or are less than) the threshold, exceeds a predetermined number, it is judged that a fault is detected.

Figure 11:
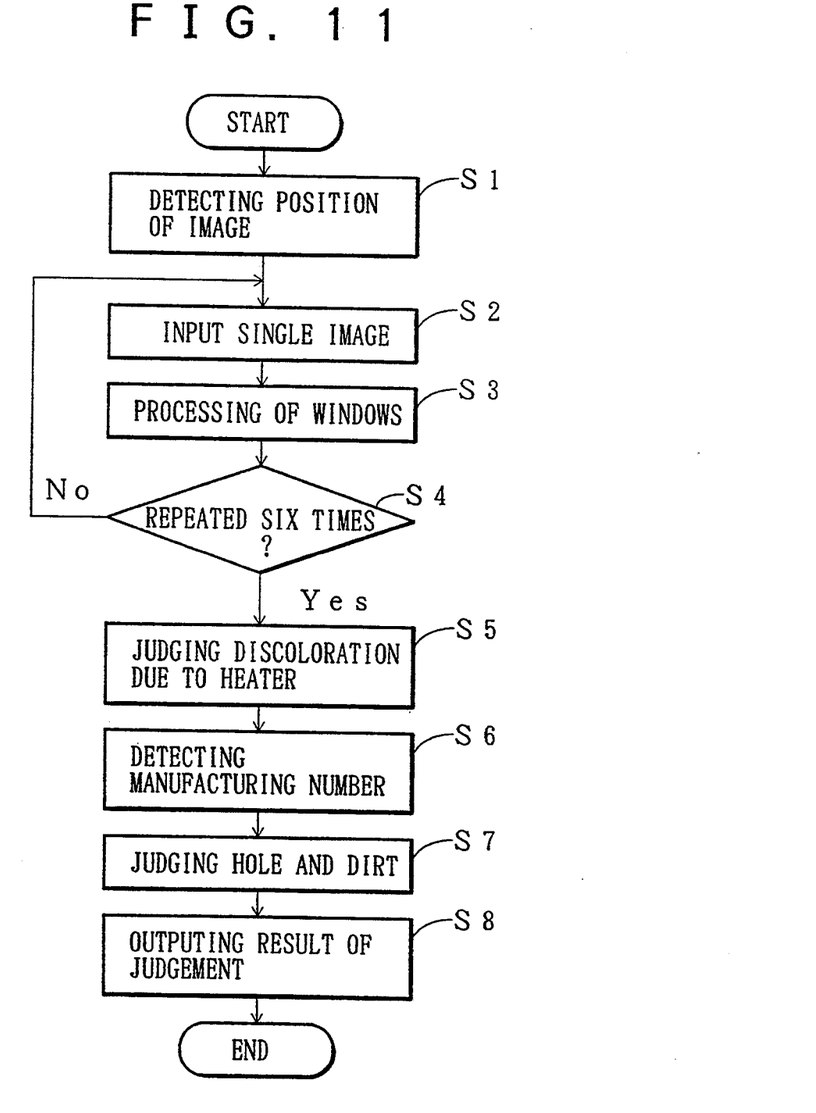
FIG. 11 is a flowchart showing image information processing and judging procedures according to the embodiment of the present invention.

FIG. 11 is a flowchart showing the processing of each of the windows. The high speed image-processing apparatus 53 starts entrapping images to switch the personal computer 54 on. Then, the position of the image of the cigarette is detected with respect to the visual field S of the CCD camera 4 based on a first image information in Step 1. The luminance information of the single image from the high speed image-processing apparatus 53 is inputted in Step 2, and the processing of each of the windows such as summing up the luminance of each of the windows is carried out in Step 3. Then, the above steps starting from the step 2 is repeated for the six imaged in accordance with the judgment in step 4.

The processing of each of the windows provides the sum of the luminance to judge the discoloration due to a heater as described above in Step 5. Then, in Step 6, the position of the manufacturing number to be masked is detected to judge the presence of a hole (pin hole or tear) or a dirt in Step 7. As a result, the result of the inspection is outputted in Step 8. The above process is repeated after a high speed image-processing apparatus 53 starts entrapping the image.

Although cigarettes are selected as inspected objects in the above embodiment, it is possible to inspect a long cylindrical object with large diameter. When a single camera cannot pick up an image, a plurality of cameras can be used for picking up the image and the images which are picked up by the cameras are combined to judge the inspected object.

As described above, in the present invention, the appearance of the cylindrical object is picked up by the camera while the image being axially divided into a plurality of images. Characters and symbols printed on an axially predetermined area of the divided images are masked to add the luminance of each of the picked up images, and the sum of the luminance is compared with a threshold to judge a defective product. Therefore, an object on which characters or symbols are printed can be checked to remove a defective product by picking up the outer periphery of the object by a single camera. Further, the threshold is to be selected in accordance with the kind of defect, and thus provides automatic detecting apparatuses for various purposes.

Further, with the detecting apparatus according to the present invention, the inspected object can be transported horizontally without a special rotating mechanism for the inspected object. That is, the inspected object can be rotated with ease by only placing the inspected object on a rotating roller having a chain-driven shaft, which provides simple transporting system.

What is claimed is:

1. An apparatus for inspecting cigarettes comprising:
   rotating means for rotating a cigarette about an axis of said cigarette;
   pick-up means for picking up images of said cigarette, said images including picture elements, each picture element having a corresponding luminance value;
   mask window generating means for generating at least one masking window to mask at least one predetermined portion of at least one image;
   image-processing means for generating at least one luminance sum for each image, said luminance sum for each image being a summation of only said luminance values for a predetermined number of picture elements in unmasked portions of said image;
   comparing means for comparing each luminance sum to a predetermined threshold; and
   judging means for judging whether said cigarette includes a defect based on a result of each comparison.

2. The apparatus of claim 1, wherein
   said image-processing means divides at least one portion of each image into windows, each window including picture elements arranged in a direction corresponding to said axis of said cigarette; said image-processing means divides each window into sub-windows; and said image-processing means generates a luminance sum corresponding to each sub-window, said luminance sum for each sub-window being a summation of only said luminance values for said picture elements included in said sub-window; and
   said comparing means compares each luminance sum of each sub-window to a second predetermined threshold;
   said apparatus further comprises counting means for generating a count for each image by counting a number of said sub-windows, for each image, which have luminance sums less than said second predetermined threshold based on results of said comparison; and
   said judging means judges a defect in said cigarette when said count exceeds a predetermined count value.

3. An apparatus for inspecting cylindrical objects comprising:
   rotating means for rotating a cylindrical object about an axis of said cylindrical object;
   pick-up means for picking up images of said cylindrical object, said pick-up means operating in cooperation with said rotating means so that said images of said cylindrical object represent an entire circumferential surface of said cylindrical object, said images including picture elements, each picture element having a corresponding luminance value;
   image-processing means for generating at least one luminance sum for each image, said luminance sum for each image being a summation of only said luminance values for a predetermined number of picture elements;
   comparing means for comparing each luminance sum to a predetermined threshold; and
   judging means for judging whether said cylindrical object includes a defect based on a result of each comparison.

4. The apparatus of claim 3, wherein said image-processing means divides at least one portion of each image into windows, each window including picture elements arranged in a direction corresponding to said axis of said cylindrical object, and said image-processing means generates a luminance sum corresponding to each window, said luminance sum for each window being a summation of only said luminance values for said picture elements included in said window.

5. An apparatus for inspecting cylindrical objects comprising:
   rotating means for rotating a cylindrical object about an axis of said cylindrical object;
   pick-up means for picking up images of said cylindrical object, said images including picture elements, each picture element having a corresponding luminance value;
   mask window generating means for generating at least one masking window to mask at least one predetermined portion of at least one image;

image-processing means for generating at least one luminance sum for each image, said luminance sum for each image being a summation of only said luminance values for a predetermined number of picture elements in unmasked portions of said image;

comparing means for comparing each luminance sum to a predetermined threshold; and judging means for judging whether said cylindrical object includes a defect based on a result of each comparison.

6. The apparatus of claim 5, wherein said pick-up means operates in cooperation with said rotating means so that said images of said cylindrical object represent an entire circumferential surface of said cylindrical object.

7. The apparatus of claim 5, wherein said image-processing means divides at least one portion of each image into windows, each window including picture elements arranged in a direction corresponding to said axis of said cylindrical object, and said image-processing means generates a luminance sum corresponding to each window, said luminance sum for each window being a summation of only said luminance values for said picture elements included in said window.

8. The apparatus of claim 7, wherein said at least one portion fails to include said at least one predetermined portion.

9. The apparatus of claim 5, wherein said image-processing means divides at least one portion of each image into windows, each window including picture elements arranged in a direction corresponding to said axis of said cylindrical object; said image-processing means divides each window into sub-windows; and said image-processing means generates a luminance sum corresponding to each sub-window, said luminance sum for each sub-window being a summation of only said luminance values for said picture elements included in said sub-window; and said comparing means compares each luminance sum of each sub-window to a second predetermined threshold;

said apparatus further comprises counting means for generating a count for each image by counting a number of said sub-windows, for each image, which have luminance sums less than said second predetermined threshold based on results of said comparison; and said judging means judges a defect in said cylindrical object when said count exceeds a predetermined count value.

10. An apparatus for inspecting cylindrical objects comprising:

rotating means for rotating a cylindrical object about an axis of said cylindrical object;

pick-up means for picking up images of said cylindrical object, said images including picture elements, each picture element having a corresponding luminance value;

mask window generating means for generating at least one masking window to mask at least one predetermined portion of at least one image;

image-processing means for dividing at least one portion of each image into windows, each window including picture elements arranged in a direction corresponding to said axis of said cylindrical object; said image-processing means for dividing each window into sub-windows; and said image-processing means for generating a luminance sum corresponding to each sub-window, said luminance sum for each sub-window being a summation of only said luminance values for said picture elements included in said sub-window; and comparing means for comparing each luminance sum of each sub-window to a predetermined threshold;

counting means for generating a count for each image by counting a number of said sub-windows, for each image, which have luminance sums less than said predetermined threshold based on results of said comparison; and judging means for judging a defect in said cylindrical object when said count exceeds a predetermined count value.

11. The apparatus of claim 10, wherein said at least one portion fails to include said at least one predetermined portion.

* * * * *